United States Patent
Neumann et al.

(10) Patent No.: US 7,078,573 B2
(45) Date of Patent: Jul. 18, 2006

(54) DEWATERING OF CIRCULATORY FLOWS IN THE PRODUCTION OF BISPHENOL A

(75) Inventors: Rainer Neumann, Bad Tölz (DE); Ulrich Blaschke, Krefeld (DE); Stefan Westernacher, Kempen (DE)

(73) Assignee: Bayer Materialscience AG, Leverkusen (DE)

( * ) Notice: Subject to any disclaimer, the term of this patent is extended or adjusted under 35 U.S.C. 154(b) by 31 days.

(21) Appl. No.: 11/043,275

(22) Filed: Jan. 26, 2005

(65) Prior Publication Data

US 2005/0177007 A1    Aug. 11, 2005

(30) Foreign Application Priority Data

Feb. 5, 2004    (DE) .................. 10 2004 005 726

(51) Int. Cl.
*C07C 39/16*    (2006.01)

(52) U.S. Cl. .................................... 568/728
(58) Field of Classification Search ................ 568/728
See application file for complete search history.

(56) References Cited

U.S. PATENT DOCUMENTS

| | | | |
|---|---|---|---|
| 4,950,804 A | 8/1990 | Iimuro et al. | 568/727 |
| 4,994,594 A | 2/1991 | Silva et al. | 558/268 |
| 5,723,688 A | 3/1998 | Patrascu et al. | 568/724 |
| 5,785,823 A * | 7/1998 | Meurer et al. | 203/71 |
| 6,586,637 B1 | 7/2003 | Iwahara | 568/728 |
| 6,653,513 B1 | 11/2003 | Iwahara | 568/728 |
| 6,723,885 B1 * | 4/2004 | Heydenreich et al. | 568/728 |
| 2003/0013925 A1 | 1/2003 | Iwahara | 568/728 |
| 2004/0030196 A1 * | 2/2004 | Saruwatari et al. | 568/728 |

OTHER PUBLICATIONS

"Kirk-Othmer Encyclopedia of Chemical Technology," 4th Ed., vol. 19, pp. 584-599 (1996)).*

* cited by examiner

*Primary Examiner*—Michael L. Shippen

(57) ABSTRACT

A process for producing bisphenol A is disclosed. The process entails a) reacting phenol with acetone in the presence of an acidic catalyst to form a reaction mixture that includes bisphenol A and water, and b) removing water from the reaction mixture by distillation in a column to obtain a bottom product, and c) separating bisphenol-A/phenol adduct from the reaction mixture by crystallization and filtration. The bottom temperature of the column is 100 to 150° C., the overhead temperature of the column is 20 to 80° C., the absolute pressure is 50 to 300 mbar at the head of the column and 100 to 300 mbar at the bottom of the column, and wherein said (c) is carried out before or after said (b).

11 Claims, No Drawings

US 7,078,573 B2

DEWATERING OF CIRCULATORY FLOWS IN THE PRODUCTION OF BISPHENOL A

FIELD OF THE INVENTION

The invention relates to bisphenol A and to a process for its preparation.

TECHNICAL BACKGROUND OF THE INVENTION

Bisphenols in the form of condensation products of phenols and carbonyl compounds are source materials or intermediate products for the manufacture of a large number of commercial products. The condensation product arising from the reaction between phenol and acetone, 2,2-bis(4-hydroxyphenyl)propane (bisphenol A, BPA), is of particular technical importance. BPA serves as source material for the production of diverse polymeric materials, such as, for example, polyarylates, polyether imides, polysulfones and modified phenol-formaldehyde resins. Preferred fields of application lie in the production of epoxy resins and polycarbonates.

Technically relevant methods for producing BPA are known and are based on the acid-catalysed conversion of phenol with acetone, wherein a phenol/acetone ratio of more than 5:1 in the reaction is preferably adjusted. Homogeneous and also heterogeneous Bronsted acids or Lewis acids may be used as acidic catalysts, for instance strong mineral acids such as hydrochloric acid or sulfuric acid. Gel-like or macroporous sulfonated cross-linked polystyrene resins (acidic ion-exchangers) are preferably used. By way of cross-linker, divinylbenzene is normally employed, but others, such as divinylbiphenyl, may also find application. In addition to the catalyst, use may be made of a co-catalyst. In this connection thiols that carry at least one SH function may be used. The co-catalyst may be either dissolved homogeneously in the reaction solution or, in the case of the acidic ion-exchangers, fixed to the catalyst itself. Homogeneous co-catalysts are, for example, mercaptopropionic acid, hydrogen sulfide, alkyl sulfides such as, for example, ethyl sulfide and similar compounds. Fixed co-catalysts are aminoalkyl thiols and pyridylalkyl thiols which are ionically bonded to the catalyst, in which case the SH function may be protected and is only set free during or after fixing to the catalyst. Similarly, the co-catalyst may be covalently bonded to the catalyst in the form of alkyl thiol or aryl thiol.

In the course of the conversion of phenol with acetone in the presence of acidic catalysts a product mixture results which, besides unconverted phenol and, where appropriate, acetone, primarily contains BPA and water. In addition to these, typical by-products of the condensation reaction arise in small quantities, for instance 2-(4-hydroxyphenyl)-2-(2-hydroxyphenyl)propane (o,p-BPA), substituted indanes, hydroxyphenyl indanols, hydroxyphenyl chromanes, substituted xanthenes and more highly condensed compounds with three or more phenyl rings in the molecular skeleton. In addition, further secondary components such as anisole, mesityl oxide, mesitylene and diacetone alcohol may be formed as a result of self-condensation of the acetone and reaction with impurities in the raw materials.

For economic and technical reasons, the reaction is usually conducted in such a way that one-hundred-percent conversion of the acetone is not obtained, and 0.1–0.6 wt. % is still contained in the outflow of the reactor.

The named by-products, such as water and unconverted feed materials phenol and acetone, impair the suitability of BPA for producing polymers and have to be separated by suitable processes. High purity demands are made of the raw material BPA, particularly for the purpose of producing polycarbonate.

One method for reprocessing and purifying BPA is undertaken by separation of BPA from the reaction mixture in the form of a roughly equimolar crystalline adduct with phenol by cooling of the reaction mixture accompanied by crystallization of the BPA/phenol adduct in a suspension crystallization. The BPA/phenol adduct crystals are then separated from the liquid phase by means of a suitable apparatus for solid/liquid separation, such as rotary filters or centrifuges, and are supplied to a further purification stage.

Adduct crystals obtained in this way typically have a purity of >99 wt. % BPA, relative to the sum of BPA and the secondary components, in the case of a phenol proportion of approx. 40 wt. %. By washing with suitable solvents, which typically contain one or more components from the group comprising acetone, water, phenol, BPA and secondary components, the adduct crystals can be freed of superficially adhering impurities.

The flow of liquid (mother liquor) resulting in the course of the solid/liquid separation contains phenol, BPA, water that has arisen in the course of the reaction, unconverted acetone, and is enriched with the secondary components typically resulting in the course of the production of BPA. This flow of mother liquor is conventionally recirculated into the reaction unit. In order to maintain the catalytic activity of the acidic ion-exchangers, resulting water is removed by distillation, whereby acetone that is still present in the given case is also removed from the mother liquor. The dewatered reaction flow which is obtained in this way is replenished with phenol and acetone and is recirculated into the reaction unit. Alternatively, water and acetone may also be removed by means of distillation prior to carrying out the suspension crystallization of the BPA/phenol adduct. In the course of the stated distillation steps, a partial quantity of the phenol that is present in the reaction solution may also be removed by means of distillation. EP-A-1 162 188 describes such a separation of the reaction water and of the incompletely reacted acetone by means of distillation.

With such a circulatory mode of operation the problem arises that by-products of the production of BPA are enriched in the circulatory flow and result in the deactivation of the catalyst system and also in inferior product quality. In order to avoid an excessive enrichment of secondary components in the circulatory flow, a partial quantity of the circulatory flow—optionally after partial or complete recovery of phenol by distillation—is extracted from the process chain in the form of so-called BPA resin.

In addition, it has proved advantageous to conduct a fraction or the total quantity of the circulatory flow, after the solid/liquid separation and before or after the separation of water and residual acetone, across a rearrangement unit filled with acidic ion-exchanger. This unit is generally operated at higher temperatures than the reaction unit. In this rearrangement unit some of the secondary components of the production of BPA which are present in the circulatory flow are isomerized under the prevailing conditions to form BPA, so that the overall yield of BPA may be increased.

The BPA/phenol adduct crystals obtained subsequent to the suspension crystallization of the reaction solution, described above, and the solid/liquid separation are supplied to ongoing purification steps, in the course of which the separation of phenol and optionally the lessening of the concentration of secondary components are achieved.

In this way, the BPA/phenol adduct crystals may be recrystallised from phenol, organic solvents, water or mixtures of the named solvents, which optionally still contain BPA and/or its isomers, by a suspension crystallisation. In this connection, the phenol that is present in the adduct crystals can also be separated entirely or partially through the choice of suitable solvents. The phenol remaining in the BPA in the given case after the recrystallisation is then separated entirely by suitable distillative, desorptive or extractive methods.

Alternatively, the phenol may also be removed from the BPA/phenol adduct crystals by means of melting-out processes. But with these processes the BPA is subjected to thermal loads, resulting in undesirable dissociations of BPA.

After the separation of phenol, a bisphenol-A melt is obtained which may be used without prior solidification for the production of polycarbonate by the transesterification process (molten polycarbonate). But the bisphenol-A melt may also be solidified, for sale or for alternate usage, by known processes, such as, for example, by the prilling process or by exfoliation. Furthermore, the melt may be dissolved in caustic-soda solution and may be employed in the polycarbonate process in accordance with the interphase process. The bisphenol A that has been freed of phenol may optionally be subjected, prior to further processing, to a purification step such as, for example, a melt crystallization, a distillation and/or a recrystallization out of phenol, water or an organic solvent such as, for example, toluene or mixtures of these substances.

Prior to being recirculated into the reaction, the mother liquor has to be dewatered, since by reason of the thermodynamic equilibrium the reaction water would greatly suppress the reaction of phenol and acetone to form bisphenol A and would consequently reduce the conversion arising from the reaction. On the other hand, the unconverted residual acetone should remain in the reaction solution, since otherwise it would have to be isolated in elaborate manner from side flows and would have to be recirculated into the reaction in order to keep losses of raw materials down for economic reasons.

The object of the present invention was therefore to make available a process for producing bisphenol A with which the reaction water may be removed from the reaction solution or from the mother liquor that stems from the crystallization and filtration, whereby the unconverted residual acetone remains largely in the reaction solution.

SUMMARY OF THE INVENTION

A process for producing bisphenol A is disclosed. The process entails a) reacting phenol with acetone in the presence of an acidic catalyst to form a reaction mixture that includes bisphenol A and water, and b) removing water from the reaction mixture by distillation in a column to obtain a bottom product, and c) separating bisphenol-A/phenol adduct from the reaction mixture by crystallization and filtration. The bottom temperature of the column is 100 to 150° C., the overhead temperature of the column is 20 to 80° C., the absolute pressure is 50 to 300 mbar at the head of the column and 100 to 300 mbar at the bottom of the column, and wherein said (c) is carried out before or after said (b).

DETAILED DESCRIPTION OF THE INVENTION

It has now been found that this object may be achieved by separation of the reaction water from the reaction solution in a vacuum distillation.

The invention relates to a process for producing bisphenol A, wherein a) phenol and acetone are converted in the presence of an acidic catalyst to form a reaction mixture containing bisphenol A and then b) water is removed from the reaction mixture by means of distillation, the distillation column that is employed being operated at a bottom temperature from 100° C. to 150° C. and at an overhead temperature from 20° C. to 80° C., and the absolute pressure amounting to 50 mbar to 300 mbar at the head of the column and to 100 mbar to 300 mbar at the bottom of the column and c) before or after the distillation in step b) a bisphenol-A/phenol adduct is separated from the reaction mixture by crystallisation and filtration.

The discovery underlying the invention is that in the course of the distillative reprocessing of the reaction mixture in a vacuum distillation for the purpose of separating water the water may be separated almost quantitatively—that is to say, in a proportion amounting to more than 95%. But, at the same time, with this vacuum distillation more than 80% of the unconverted acetone introduced into the distillation preferably remains in the bottom product. Furthermore, the bottom product preferably contains between 0.01 wt. % and 0.2 wt. % water (relative to the bottom product). To this end, the distillation column that is employed is operated with a bottom temperature from 100° C. to 150° C., preferably 110° C. to 140° C., particularly preferably 125° C. to 135° C., and with an overhead temperature from 20° C. to 80° C., preferably 30° C. to 70° C., particularly preferably 50° C. to 60° C. The vacuum in the head of the column amounts to 50 mbar to 300 mbar, preferably 80 mbar to 200 mbar, particularly preferably 100 mbar to 150 mbar. The bottom vacuum amounts to 100 mbar to 300 mbar, preferably 120 mbar to 250 mbar, particularly preferably 150 mbar to 200 mbar. By way of separation processes for achieving the stated object, those distillation devices known to a person skilled in the art may be employed which contain internal fittings such as, for example, filling materials and/or packings and/or trays.

The bottom product that is obtained in the course of distillation is suitable, optionally after separation of the bisphenol-A/phenol adduct crystals by a suspension crystallization, for re-use in the reaction after replenishment of the consumed components phenol and acetone and also, where appropriate, co-catalyst, whereby the consumed phenol may be replenished entirely or in part also prior to distillation. A further advantage of the process according to the invention is that degradation compounds of the sulfur-containing co-catalyst, such as, for example, mercaptopropionic acid, and of the sulfo-acidic ion-exchanger are likewise separated overhead with the reaction water and in the course of a recirculation of the bottom product into the reaction consequently do not disrupt the reaction, mostly in the course of the later separation of the bisphenol A. Similarly, in this case it is possible for impurities to be separated overhead from the raw materials that are employed, such as methanol and also by-products arising in the course of the production of bisphenol A, such as anisole from methanol and phenol, as well as the compounds arising from the self-condensation of acetone, such as, for example, mesitylene, mesityl oxide and diacetone alcohol, at least in part but preferably in a proportion amounting to at least 50%. In the case where use is made of mercaptopropionic acid by way of co-catalyst, the co-catalyst remains in the bottom product. Only the decomposed portion and the portion that has been lost as a result of the discharge from the circuit have to be replenished in order to conduct the reaction with a constant content of co-catalyst.

The bisphenol A that is produced by the process according to the invention is preferably converted into polycarbonate with phosgene in accordance with the interphase process or with diaryl carbonates, preferably diphenyl carbonate, in accordance with the melt process.

EXAMPLES

Example 1

On a sulfo-acidic ion-exchanger 4 wt. % acetone are converted into bisphenol A with 96 wt. % mother liquor (6 wt. % isomers, 7 wt. % bisphenol A, 0.05 wt. % water, 300 ppm mercaptopropionic acid and approx. 83 wt. % phenol). In this process a reaction mixture results containing 1 wt. % reaction water and 0.3 wt. % unreacted acetone. After crystallization and separation of the bisphenol-A/phenol adduct crystals the remaining mother liquor is supplied to a vacuum-distillation stage. The bottom temperature amounts to 130° C.; the overhead temperature amounts to 54° C. The vacuum in the bottom amounts to 163 mbar, in the head to 129 mbar. In the process, over 95% of the reaction water introduced into the column is condensed at the head; the residue remains in the bottom product. In the overhead product, in addition to the water, 5 wt. % phenol and 5 wt. % acetone are found, relative to the overhead product. In addition to these, anisole and methanol, as well as self-condensation products of acetone, such as, for example, mesitylene and diacetone alcohol, are detected in the overhead product. A strongly sulfurous odor indicates that degradation products of the ion-exchanger and of the mercaptopropionic acid are likewise removed from the mother liquor. In the bottom there remain 0.27 wt. % acetone and 0.05 wt. % water, relative to the bottom product in the mother liquor which is again enriched with acetone to 4 wt. % and. with phenol to 83 wt. % and also with mercaptopropionic acid to 300 ppm and is conducted back into the reaction. The BPA resulting from this process is suitable, after washing of the mixed crystals and separation of the phenol, for the production of polycarbonate both in accordance with the interphase process and in accordance with the transesterification(-melt) process.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing bisphenol A comprising
   (a) reacting phenol with acetone in the presence of acidic catalyst to form a reaction mixture containing bisphenol A and water,
   b) removing the water by distillation in a distillation column, and obtaining a bottom product,
   c) separating bisphenol-A/phenol adduct crystals from the reaction mixture by crystallization and filtration,
   wherein the bottom temperature of the column is 100 to 150° C., the overhead temperature of the column is 20 to 80° C., the absolute pressure is 50 to 300 mbar at the head of the column and 100 to 300 mbar at the bottom of the column, and wherein said (c) is carried out before or after said (b).

2. The process according to claim 1 wherein the acidic catalyst is a sulfo-acidic ion-exchanger.

3. The process of claim 2 wherein the sulfo-acidic ion-exchanger is used in conjunction with a co-catalyst.

4. The process according to claim 1 further comprising re-circulating the bottom product into said a).

5. The process of claim 4 wherein the re-circulating is subsequent to said c).

6. The process according to claim 4, wherein the bottom product is enriched with acetone, phenol and optionally with a co-catalyst.

7. The process according to claim 1 wherein at least 95% of the water present in the reaction mixture is separated in the course of said (b).

8. The process according to claim 1 wherein the bottom product obtained in step b) contains at least 80% of the unconverted acetone of step a) introduced into the distillation of step b).

9. The process according to claim 1 wherein the bottom product obtained in step b) contains at least 80% of the unconverted acetone of step a) introduced into the distillation of step b) and between 0.01 wt. % and 0.2 wt. % water, relative to the bottom product.

10. The process according to claim 1 wherein the bottom product obtained in step b) contains at most 50% of the impurities methanol, anisole and the self-condensation production of acetone which have been introduced into the distillation.

11. The process according to claim 2 sulfur-containing degradation products of the sulfo-acidic ion-exchanger and/or of the sulfur-containing co-catalyst are distilled off overhead in step b).

* * * * *